US007128915B2

(12) United States Patent
Hernandez et al.

(10) Patent No.: US 7,128,915 B2
(45) Date of Patent: Oct. 31, 2006

(54) MEMBRANE VIRUS HOST RANGE MUTATIONS AND THEIR USES AS VACCINE SUBSTRATES

(75) Inventors: Racquel Hernandez, Raleigh, NC (US); Dennis T. Brown, Raleigh, NC (US)

(73) Assignee: Research Development Foundation, Carson City, NV (US)

( * ) Notice: Subject to any disclaimer, the term of this patent is extended or adjusted under 35 U.S.C. 154(b) by 139 days.

(21) Appl. No.: 09/952,782

(22) Filed: Sep. 12, 2001

(65) Prior Publication Data

US 2002/0106379 A1  Aug. 8, 2002

Related U.S. Application Data

(63) Continuation-in-part of application No. 09/447,103, filed on Nov. 22, 1999, now Pat. No. 6,589,533, which is a continuation-in-part of application No. 09/157,270, filed on Sep. 18, 1998, now Pat. No. 6,306,401.

(51) Int. Cl.
*A61K 39/12* (2006.01)

(52) U.S. Cl. ............................. 424/199.1; 424/218.1; 435/69.7; 435/320.1

(58) Field of Classification Search ............. 424/199.1, 424/218.1; 435/69.7, 320.1
See application file for complete search history.

(56) References Cited

U.S. PATENT DOCUMENTS 6,306,401 B1 * 10/2001 Brown et al. ............ 424/218.1
6,589,533 B1 * 7/2003 Brown et al. ............ 424/205.1

OTHER PUBLICATIONS

Murphy, F. A., 1996, "Virus taxonomy", in *Fields Virology, Third Edition*, Fields, B. N., et al., eds., Lippincott-Raven Publishers, Philadelphia, pp. 24, 26-29.*
Presley, J. F., et al., 1991, "Proteolytic processing of the Sindbis virus membrane protein precursor PE2 is nonessential for growth in vertebrate cells but is required for efficient growth in invertebrate cells", J. Virol. 65(4):1905-1909.*
Lee, H., and D. T. Brown, 1994, "Mutations in an exposed domain of Sindbis virus capsid protein result in the production of noninfectious virions and morphological variants", Virol. 202:390-400.*
Hernandez, R., et al., 2000, "A single deletion in the membrane proximal region of the Sindbis virus glycoprotein E2 endodomain blocks virus assembly", J. Virol. 74(9):4220-4228.*
De Beeck, A., et al., 2003, "Role of the transmembrane domains of prM and E proteins in the formation of yellow fever virus envelope", J. Virol. 77(2):813-820.*
Strauss, E. G., et al., 2002, "Molecular genetic evidence that the hydrophobic anchors of glycoproteins E2 and E1 interact during assembly of alphaviruses", J. Virol. 76(20):10188-10194.*
Cocquerel, L., et al., 2000, "Charged residues in the transmembrane domains of hepatitis C virus glycoproteins play a major role in the processing . . . ", J. Virol. 74(8):3623-3633.*
Allison, S. L., et al., 1999, "Mapping of functional elements in the stem-anchor region of tick-borne encephalitis virus envelope protein E", J. Virol. 73(7):5605-5612.*
Yao, J., and S. Gillam, 1999, "Mutational analysis, using a full-length rubella virus cDNA clone, of rubella virus E1 transmembrane and cytoplasmic . . . ", J. Virol. 73(6):4622-4630.*
Adams and Rose, "Structural requirements of a membrane-spanning domain for protein anchoring and cell surface transport", *Cell*, 41:1007-1015, 1985.
Clayton, "The utilization of sterols by insects", *Journal of Lipid Research*, 5:3-19, 1964.
Hernandez et al., "Deletions in the transmembrane domain of a sindbis virus glycoprotein alter virus infectivity, stability, and host range", *Journal of Virology*, 77:12710-12719, 2003.
Mitsuhashi et al., "Sterol-free eukaryotic cells from continuous lines of insects", *Cell Biology International Reports*, 7:1057-1062, 1983.
Rice, "Isolation and characterization of the hydrophobic COOH-terminal domains of the sindbis virion glycoproteins", *J. Mol. Biol.* 154:355-378, 1982.
West et al., "Mutations in the endodomain of sindbis virus glycoprotein E2 define domains critical for viruses assembly", *Department of Molecular & Structural Biochemistry: North Carolina State University*, 1-29 (submitted).
Bridgen and Elliott, "Resue of a segmented negative-strand RNA virus entirely from cloned complementary DNAs," *Proc. Natl. Acad. Sci. USA*, 93:15400-15404, 1996.
Lai et al., "Infectious RNA transcribed from stably cloned full-length cDNA of dengue type 4 virus," *Proc. Natl. Acad. Sci. USA*, 88:5139-5143, 1991.

* cited by examiner

*Primary Examiner*—Jeffrey S. Parkin
(74) *Attorney, Agent, or Firm*—Fulbright & Jaworski LLP

(57) ABSTRACT

The present invention is directed to genetically engineered, membrane-enveloped viruses with deletion mutations in the protein transmembrane domains. Also provided are viral vaccines based on the engineered viruses, methods of producing and using such vaccines.

13 Claims, 7 Drawing Sheets

Figure 4

```
nt9717                                                                              nt9800
CATCCTGTGTACACCATCTTAGCCGTCGCATCAGCTACCGTGGGATGATGATTGGCGTAACTGTTGCAGTGTTATGTGCCTGT
 H  P  V  Y  T  I  L  A  V  A  S  A  T  V  A  M  M  I  G  V  T  V  A  V  L  C  A  C
```

| Alignment variants | SEQ ID No. |
|---|---|
| (consensus above) | 20 |
| | 21 |
| — — — — — — — — — — — — — — — M — — — — — — — — — — — | 22 (TM25) |
| — — — — — — — — — — — — — — — M — — — — — — — — — — — | 23 (TM24) |
| — — — — — — — — — — — — — — — M M — — — — — — — — — — | 24 (TM23) |
| — — — — — — — — — — — — V A M M — — — — — — — — — — — | 25 (TM22) |
| — — — — — — — — — — — — V A M M I — — — — — — — — — — | 26 (TM21) |
| — — — — — — — — — — — — V A M M I G — — — — — — — — — | 27 (TM20) |
| — — — — — — — A S A T — V A M M — — — — — — — — — — — | 28 (TM19) |
| — — — — — — — A S A T — V A M M — — — — — — — — — — — | 29 (TM18) |
| — — — — — — — A S A T — V A M M — — — — — — — — — — — | 30 (TM17) |
| — — — — — — — S A T — V A M M — G — — — — — T — — — V | 31 (TM16) |
| — — — — — — — A S A T — V A M M — G V T — — T — — — V | 32 (TM14) |
| — — — — — — — A S A T — V A M M — G V T — — T — — — V | 33 (TM13) |
| — — — — L — — A V A S — V A M M — G V T — — V — — — V | 34 (TM10) | ically engineered membrane-enveloped

SEQUENCE LISTING

```
<160> NUMBER OF SEQ ID NOS: 34

<210> SEQ ID NO 1
<211> LENGTH: 30
<212> TYPE: DNA
<213> ORGANISM: artificial sequence
<220> FEATURE:
<223> OTHER INFORMATION: Used as the mutagenesis primer with the
      "forward primer" to generate a 518 base "Megaprimer"
      corresponding to nucleotides 9295-9813.

<400> SEQUENCE: 1
ctcacggcgc gcacaggcac ataacactgc                                       30

<210> SEQ ID NO 2
<211> LENGTH: 18
<212> TYPE: DNA
<213> ORGANISM: artificial sequence
<220> FEATURE:
<223> OTHER INFORMATION: Used as the "forward primer" with the
      mutagenesis primer to generate a 518 base megaprimer
      corresponding to nucleotides 9295-9813.

<400> SEQUENCE: 2
ccatcaagca gtgcgtcg                                                    18

<210> SEQ ID NO 3
<211> LENGTH: 25
<212> TYPE: DNA
<213> ORGANISM: artificial sequence
<220> FEATURE:
<223> OTHER INFORMATION: Used as the "reverse primer" with the
      megaprimer and the Toto 1101 plasmid template to create 1149
      nucleotide product used to create the deletion
      mutant K391 in Toto 1101.

<400> SEQUENCE: 3
ggcagtgtgc accttaatcg cctgc                                            25

<210> SEQ ID NO 4
<211> LENGTH: 26
<212> TYPE: PRT
<213> ORGANISM: Sindbis virus
<220> FEATURE:
<221> NAME/KEY: transmembrane domain of E2 in the PE2 sequence
<222> LOCATION: 365..390

<400> SEQUENCE: 4

Val Tyr Thr Ile Leu Ala Val Ala Ser Ala Thr Val Ala Met Met
                 5                  10                  15

Ile Gly Val Thr Val Ala Val Leu Cys Ala Cys
             20                  25

<210> SEQ ID NO 5
<211> LENGTH: 21
<212> TYPE: DNA
```

```
<213> ORGANISM: artificial sequence
<220> FEATURE:
<222> LOCATION: 9306-9327
<223> OTHER INFORMATION: Forward primer E1Bcl21 from megaprimer used
      with reverse primer to generate deletion constructs
      containing unique BclI and SplI sites.

<400> SEQUENCE: 5
gcgtcgccta taagagcgac c                                              21

<210> SEQ ID NO 6
<211> LENGTH: 23
<212> TYPE: DNA
<213> ORGANISM: artificial sequence
<220> FEATURE:
<222> LOCATION: 10420-10444
<223> OTHER INFORMATION: Reverse primer Splext from megaprimer used with
      forward primer to generate deletion constructs
      containing unique BclI and SplI sites.

<400> SEQUENCE: 6
cagtgtgcac cttaatcgcc tgc                                            23

<210> SEQ ID NO 7
<211> LENGTH: 24
<212> TYPE: DNA
<213> ORGANISM: artificial sequence
<220> FEATURE:
<223> OTHER INFORMATION: Mutagenic primer E2 TM10 (negative strand) used
      to create a deletion in the E2 transmembranal
      domain in the Sindbis viral glycoprotein.

<400> SEQUENCE: 7
acataacact gcgatggtgt acac                                           24

<210> SEQ ID NO 8
<211> LENGTH: 23
<212> TYPE: DNA
<213> ORGANISM: artificial sequence
<220> FEATURE:
<223> OTHER INFORMATION: Mutagenic primer E2 TM12 (negative strand) used
      to create a deletion in the E2 transmembranal domain
      in the Sindbis viral glycoprotein.

<400> SEQUENCE: 8
acataacact gcggctaaga tgg                                            23

<210> SEQ ID NO 9
<211> LENGTH: 22
<212> TYPE: DNA
<213> ORGANISM: artificial sequence
<220> FEATURE:
<223> OTHER INFORMATION: Mutagenic primer E2 TM14 (negative strand) used
      to create a deletion in the E2 transmembranal domain
      in the Sindbis viral glycoprotein.

<400> SEQUENCE: 9
acataacact gctgcgacgg ct                                             22

<210> SEQ ID NO 10
<211> LENGTH: 21
<212> TYPE: DNA
<213> ORGANISM: artificial sequence
<220> FEATURE:
<223> OTHER INFORMATION: Mutagenic primer E2 TM16 (negative strand) used
      to create a deletion in the E2 transmembranal domain
      in the Sindbis viral glycoprotein.

<400> SEQUENCE: 10
```

```
gcaacagtta cgacggctaa g                                              21
```

<210> SEQ ID NO 11
<211> LENGTH: 21
<212> TYPE: DNA
<213> ORGANISM: artificial sequence
<220> FEATURE:
<223> OTHER INFORMATION: Mutagenic primer E2 TM17 (negative strand) used
      to create a deletion in the E2 transmembranal domain
      in the Sindbis viral glycoprotein.

<400> SEQUENCE: 11

```
acagttacgc cgacggctaa g                                              21
```

<210> SEQ ID NO 12
<211> LENGTH: 21
<212> TYPE: DNA
<213> ORGANISM: artificial sequence
<220> FEATURE:
<223> OTHER INFORMATION: Mutagenic primer E2 TM18 (negative strand) used
      to create a deletion in the E2 transmembranal domain
      in the Sindbis viral glycoprotein.

<400> SEQUENCE: 12

```
gttacgccaa tgacggctaa g                                              21
```

<210> SEQ ID NO 13
<211> LENGTH: 21
<212> TYPE: DNA
<213> ORGANISM: artificial sequence
<220> FEATURE:
<223> OTHER INFORMATION: Mutagenic primer E2 TM19 (negative strand) used
      to create a deletion in the E2 transmembranal domain
      in the Sindbis viral glycoprotein.

<400> SEQUENCE: 13

```
cgccaatcat gacggctaag a                                              21
```

<210> SEQ ID NO 14
<211> LENGTH: 20
<212> TYPE: DNA
<213> ORGANISM: artificial sequence
<220> FEATURE:
<223> OTHER INFORMATION: Mutagenic primer E2 TM20 (negative strand) used
      to create a deletion in the E2 transmembranal domain
      in the Sindbis viral glycoprotein.

<400> SEQUENCE: 14

```
gcaacagtta cggtagctga                                                20
```

<210> SEQ ID NO 15
<211> LENGTH: 18
<212> TYPE: DNA
<213> ORGANISM: artificial sequence
<220> FEATURE:
<223> OTHER INFORMATION: Mutagenic primer E2 TM21 (negative strand) used
      to create a deletion in the E2 transmembranal domain
      in the Sindbis viral glycoprotein.

<400> SEQUENCE: 15

```
agttacgccg gtagctga                                                  18
```

<210> SEQ ID NO 16
<211> LENGTH: 21
<212> TYPE: DNA
<213> ORGANISM: artificial sequence
<220> FEATURE:

```
<223> OTHER INFORMATION: Mutagenic primer E2 TM22 (negative strand) used
      to create a deletion in the E2 transmembranal domain
      in the Sindbis viral glycoprotein.

<400> SEQUENCE: 16
tgcaacagtt accgccacgg t                                              21

<210> SEQ ID NO 17
<211> LENGTH: 20
<212> TYPE: DNA
<213> ORGANISM: artificial sequence
<220> FEATURE:
<223> OTHER INFORMATION: Mutagenic primer E2 TM23 (negative strand) used
      to create a deletion in the E2 transmembranal domain
      in the Sindbis viral glycoprotein.

<400> SEQUENCE: 17
acagttacgc ccgccacggt                                                20

<210> SEQ ID NO 18
<211> LENGTH: 20
<212> TYPE: DNA
<213> ORGANISM: artificial sequence
<220> FEATURE:
<223> OTHER INFORMATION: Mutagenic primer E2 TM24 (negative strand) used
      to create a deletion in the E2 transmembranal domain
      in the Sindbis viral glycoprotein.

<400> SEQUENCE: 18
gttacgccaa tcgccacggt                                                20

<210> SEQ ID NO 19
<211> LENGTH: 20
<212> TYPE: DNA
<213> ORGANISM: artificial sequence
<220> FEATURE:
<223> OTHER INFORMATION: Mutagenic primer E2 TM25 (negative strand) used
      to create a deletion in the E2 transmembranal domain
      in the Sindbis viral glycoprotein.

<400> SEQUENCE: 19
acgccaatca tcgccacggt                                                20

<210> SEQ ID NO 20
<211> LENGTH: 84
<212> TYPE: DNA
<213> ORGANISM: Sindbis virus
<220> FEATURE:
<221> NAME/KEY: nucleotide sequence of the E2 transmembranal
      domain of the Sindbis viral glycoprotein
<222> LOCATION: 9717..9800

<400> SEQUENCE: 20
catcctgtgt acaccatctt agccgtcgca tcagctaccg tggcgatgat               50
gattggcgta actgttgcag tgttatgtgc ctgt                                84

<210> SEQ ID NO 21
<211> LENGTH: 28
<212> TYPE: PRT
<213> ORGANISM: Sindbis virus
<220> FEATURE:
<221> NAME/KEY: amino acid sequence of the E2 transmembranal
      domain of the Sindbis viral glycoprotein
<222> LOCATION: 363..390

<400> SEQUENCE: 21

His Pro Val Tyr Thr Ile Leu Ala Val Ala Ser Ala Thr Val Ala
```

```
                       5                  10                  15
Met Met Ile Gly Val Thr Val Ala Val Leu Cys Ala Cys
                      20                  25

<210> SEQ ID NO 22
<211> LENGTH: 27
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acid 378, the resulting deletion mutant is TM25.

<400> SEQUENCE: 22

His Pro Val Tyr Thr Ile Leu Ala Val Ala Ser Ala Thr Val Ala
                       5                  10                  15
Met Ile Gly Val Thr Val Ala Val Leu Cys Ala Cys
                      20                  25

<210> SEQ ID NO 23
<211> LENGTH: 26
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 378 and 379, the resulting deletion mutant
      is TM24

<400> SEQUENCE: 23

His Pro Val Tyr Thr Ile Leu Ala Val Ala Ser Ala Thr Val Ala
                       5                  10                  15
Ile Gly Val Thr Val Ala Val Leu Cys Ala Cys
                      20                  25

<210> SEQ ID NO 24
<211> LENGTH: 25
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 378 through 380, the resulting deletion
      mutant is TM23

<400> SEQUENCE: 24

His Pro Val Tyr Thr Ile Leu Ala Val Ala Ser Ala Thr Val Ala
                       5                  10                  15
Gly Val Thr Val Ala Val Leu Cys Ala Cys
                      20                  25

<210> SEQ ID NO 25
<211> LENGTH: 24
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 378 through 381, the resulting deletion
      mutant is TM22.

<400> SEQUENCE: 25

His Pro Val Tyr Thr Ile Leu Ala Val Ala Ser Ala Thr Val Ala
                       5                  10                  15
Val Thr Val Ala Val Leu Cys Ala Cys
                      20
```

<210> SEQ ID NO 26
<211> LENGTH: 23
<212> TYPE: PRT
<213> ORGANISM: artificial sequence
<220> FEATURE:
<223> OTHER INFORMATION: Sequence of the E2 transmembranal domain
    of the Sindbis viral glycoprotein after deleting
    amino acids 376 through 380, the resulting
    deletion mutant is TM21.

<400> SEQUENCE: 26

His Pro Val Tyr Thr Ile Leu Ala Val Ala Ser Ala Thr Gly Val
              5                  10                  15

Thr Val Ala Val Leu Cys Ala Cys
            20

<210> SEQ ID NO 27
<211> LENGTH: 22
<212> TYPE: PRT
<213> ORGANISM: artificial sequence
<220> FEATURE:
<223> OTHER INFORMATION: Sequence of the E2 transmembranal domain of the
    Sindbis viral glycoprotein after deleting amino
    acids 376 through 381, the resulting deletion
    mutant is TM20.

<400> SEQUENCE: 27

His Pro Val Tyr Thr Ile Leu Ala Val Ala Ser Ala Thr Val Thr
              5                  10                  15

Val Ala Val Leu Cys Ala Cys
            20

<210> SEQ ID NO 28
<211> LENGTH: 21
<212> TYPE: PRT
<213> ORGANISM: artificial sequence
<220> FEATURE:
<223> OTHER INFORMATION: Sequence of the E2 transmembranal domain of the
    Sindbis viral glycoprotein after deleting amino
    acids 372 through 378, the resulting deletion
    mutant is TM19.

<400> SEQUENCE: 28

His Pro Val Tyr Thr Ile Leu Ala Val Met Ile Gly Val Thr Val
              5                  10                  15

Ala Val Leu Cys Ala Cys
            20

<210> SEQ ID NO 29
<211> LENGTH: 20
<212> TYPE: PRT
<213> ORGANISM: artificial sequence
<220> FEATURE:
<223> OTHER INFORMATION: Sequence of the E2 transmembranal domain of the
    Sindbis viral glycoprotein after deleting amino
    acids 372 through 379, the resulting deletion
    mutant is TM18.

<400> SEQUENCE: 29

His Pro Val Tyr Thr Ile Leu Ala Val Ile Gly Val Thr Val Ala
              5                  10                  15

Val Leu Cys Ala Cys
            20

<210> SEQ ID NO 30

```
<211> LENGTH: 19
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 372 through 380, the resulting deletion
      mutant is TM17.

<400> SEQUENCE: 30

His Pro Val Tyr Thr Ile Leu Ala Val Gly Val Thr Val Ala Val
                 5                  10                  15

Leu Cys Ala Cys

<210> SEQ ID NO 31
<211> LENGTH: 18
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 372 through 381, the resulting deletion
      mutant is TM16.

<400> SEQUENCE: 31

His Pro Val Tyr Thr Ile Leu Ala Val Val Thr Val Ala Val Leu
                 5                  10                  15

Cys Ala Cys

<210> SEQ ID NO 32
<211> LENGTH: 16
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 373 through 384, the resulting deletion
      mutant is TM14.

<400> SEQUENCE: 32

His Pro Val Tyr Thr Ile Leu Ala Val Ala Ala Val Leu Cys Ala
                 5                  10                  15

Cys

<210> SEQ ID NO 33
<211> LENGTH: 14
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 371 through 384, the resulting deletion mutant
      is TM12.

<400> SEQUENCE: 33

His Pro Val Tyr Thr Ile Leu Ala Ala Val Leu Cys Ala Cys
                 5                  10

<210> SEQ ID NO 34
<211> LENGTH: 12
<212> TYPE: PRT
<213> ORGANISM: artificial sequence
<220> FEATURE:
<223> OTHER INFORMATION: Sequence of the E2 transmembranal domain of the
      Sindbis viral glycoprotein after deleting amino
      acids 369 through 384, the resulting deletion mutant
      is TM10.
```

```
-continued

<400> SEQUENCE: 34

His Pro Val Tyr Thr Ile Ala Val Leu Cys Ala Cys
                5                  10
```

MEMBRANE VIRUS HOST RANGE MUTATIONS AND THEIR USES AS VACCINE SUBSTRATES

CROSS REFERENCE TO RELATED APPLICATION

This patent application is a continuation-in-part of U.S. application Ser. No. 09/447,103, filed Nov. 22, 1999, now U.S. Pat. No. 6,589,533, which is a continuation-in-part of U.S. application Ser. No. 09/157,270, filed Sep. 18, 1998, now U.S. Pat. No. 6,306,401.

FEDERAL FUNDING LEGEND

This invention was produced in part using funds obtained through a grant from the National Institutes of Health. Consequently, the federal government has certain rights in this invention.

The United States government may own certain rights to this invention pursuant to grant number AI 42775 from the National Institutes of Health.

BACKGROUND OF THE INVENTION

1. Field of the Invention

The present invention relates generally to virology and disease control. More specifically, the present invention relates to mutated arthropod vectored viruses and their uses, for example, as vaccines.

2. Description of the Related Art

Arthropod vectored viruses (Arboviruses) are viral agents which are transmitted in nature by blood sucking insects. Arboviruses include members of the alpha-, flavi- and bunya-viridae. Over 600 of these viruses are presently known and emerging members of these families are being described annually. Collectively, the arthropod vectored viruses are second only to malaria as a source of insect-transmitted disease and death in man and animals throughout the world (Berge A. O. 1975). Among these viral agents are Eastern, Western, and Venezuelan Equine Encephalitis Viruses, Dengue Fever, Japanese Encephalititis, San Angelo Fever, West Nile Fever and Yellow Fever. Furthermore, diseases caused by these agents are in resurgence in North America (*NIAID Report of the Task Force on Microbiology and Infectious Diseases* 1992, NIH Publication No. 92-3320) as a result of the introduction of the mosquito vector Aedes albopictus (Sprenger, and Wuithiranyagool 1985).

By their very nature, Arboviruses must be able to replicate in the tissues of both the invertebrate insect and the mammalian host (Brown, D. T., and L. Condreay, 1986, Bowers et al. 1995). Differences in the genetic and biochemical environment of these two host cell systems provide a basis for the production of host range mutant viruses which can replicate in one host but not the other.

Currently, Dengue Fever and Eastern Equine Encephalitis and other insect borne viruses are in resurgence in the United States. The U.S. Army and other government agencies have been trying to make vaccines against these viruses since the 1960s with little success. Thus, the prior art is deficient in a vaccine against most arthropod vectored viruses and other membrane-coated viruses. The present invention fulfills this long-standing need and desire in the art.

SUMMARY OF THE INVENTION

Viruses which are transmitted in nature by blood sucking insects are a major source of disease in man and domestic animals. Many of these viruses have lipid membrane bilayers with associated integral membrane proteins as part of their three dimensional structure. These viruses are hybrid structures in which the proteins are provided by the genetic information of the virus and the membrane is the product of the host cell in which the virus is grown. Differences in the composition of the membranes of the mammalian and insect host are exploited to produce virus mutants containing deletions in the membrane spanning domains of the virus membrane proteins. Some of the mutants are capable of replicating and assembling normally in the insect host cell but assemble poorly in the mammalian host cell. These host range mutants produce immunity to wild type virus infection when used as a vaccine in mice, and represent a novel strategy for the production of vaccines against arthropod vectored, membrane containing viruses.

In one embodiment of the present invention, there is provided a genetically engineered membrane-enveloped virus comprising a viral transmembrane glycoprotein that is able to span or correctly integrate into the membrane of insect cells but not that of mammalian cells due to deletion of one or more amino acids in the viral transmembrane glycoprotein. The virus is capable of infecting and producing progeny virus in insect cells, and is capable of infecting but not producing progeny virus in mammalian cells. The virus can be an Arthropod vectored virus such as Togaviruses, Flaviviruses, Bunya viruses and all other enveloped viruses which can replicate naturally in both mammalian and insect cells, as well a s enveloped viruses which can be made to replicate in mammalian and insect cells by genetic engineering of either the virus or the cell. Representative examples of such engineered viruses are ΔK391 virus, TM17 virus and TM16 virus.

In another embodiment of the present invention, there is provided a method of producing a viral vaccine by introducing the engineered virus disclosed herein into insect cells and allowing the virus to replicate in the insect cells to produce a viral vaccine. Representative examples of the engineered viruses are ΔK391 virus, TM 17 virus and TM16 virus.

In still another embodiment of the present invention, there is provided a method for vaccinating an individual in need of such treatment comprising the step of introducing the viral vaccine of the present invention into the individual to produce viral proteins for immune surveillance and stimulate immune system for antibody production.

In still yet another embodiment of the present invention, there is provided a method of producing a viral vaccine to a disease spread by a wild mosquito population to mammals, comprising the steps of engineering a deletion of one or more amino acids in a viral transmembrane protein to produce an engineered virus similar to TM16, TM17 or delta K391, wherein the transmembrane protein is able to span the membrane envelope in mosquito cells but not in mammalian cells; introducing the engineered virus into the wild mosquito population; and allowing the engineered virus to replicate in cells of the wild mosquito population to produce a population of mosquitoes which excludes the wild type pathogenic virus and harbors the vaccine strain of the virus so that a mosquito bite delivers the vaccine to the mammal bitten. Presence of the mutated virus renders the mosquito incapable of transmitting other membrane containing viruses (Karpf et al 1997).

Other and further aspects, features, and advantages of the present invention will be apparent from the following description of one of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 4 shows the deleted amino acids in the E2 transmembranal domain. The deleted sequence is shown under the appropriate amino acid, ranging from 1 to 16 deletions. Histidine and Proline sequences beginning at nt 9717 are on the lumenal side of the protein but are used to design the mutagenic primers.

DETAILED DESCRIPTION OF THE INVENTION

Figure 1:
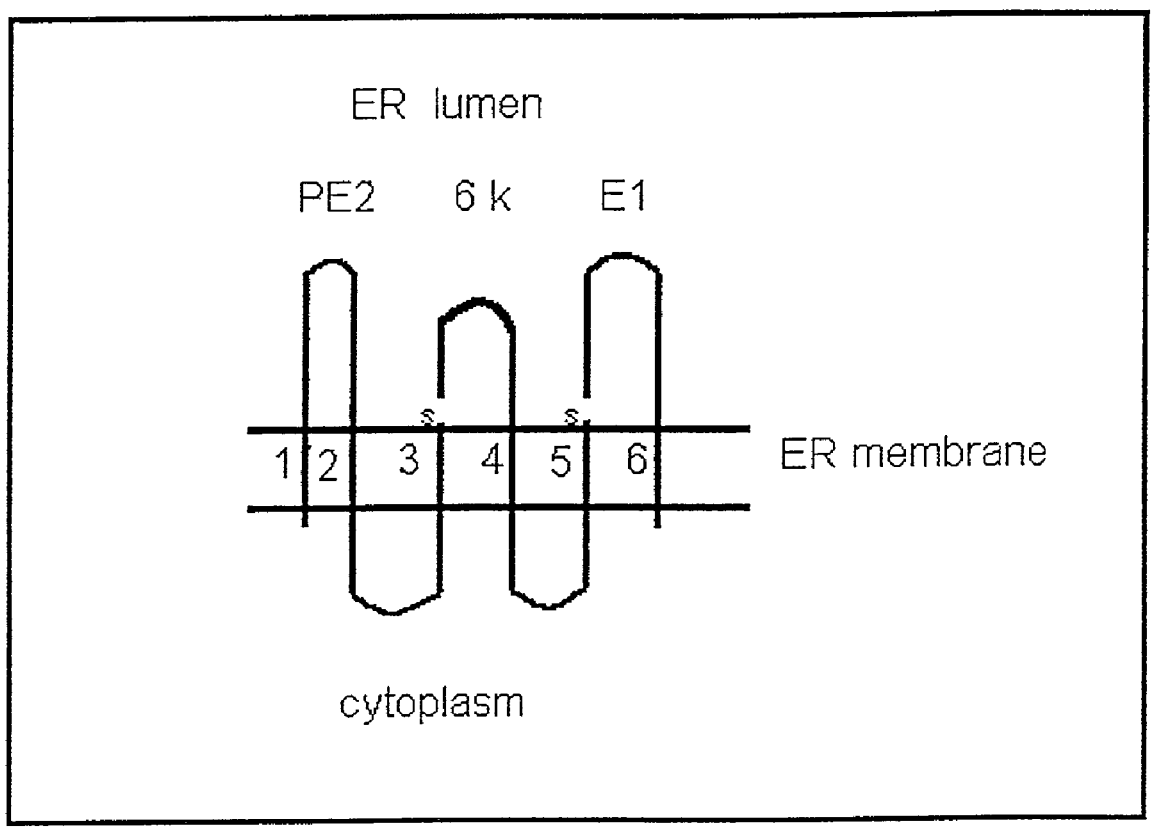
FIG. 1 shows the configuration of Sindbis virus glycoproteins after integration into the ER. The protein is a multipass protein with 6 membrane spanning domains (numbered 1–6). 1. The signal sequence for initial integration; 2. The first E2 transmembrane domain (TMD); 3. The second E2 transmembrane domain; 4. The first 6k TMD; 5. The second 6k transmembrane domain; and 6. The E1 transmembrane domain. S=point of cleavage by signal peptidase.

It will be apparent to one skilled in the art that various substitutions and modifications may be made to the invention disclosed herein without departing from the scope and spirit of the invention.

As used herein, the term "membrane-bound virus" refers to a virus which contains a lipid membrane bilayer as part of its protective exterior coat.

As used herein the term "viral envelope" refers to the lipid membrane component of the membrane containing virus and its associated proteins.

As used herein, the terms "arthropod vectored virus" or "Arbovirus" refer to viral agents which replicate and produce progeny virus in arthropod (insect) or mammalian cells. This includes Togaviruses, Flaviviruses and Bunyaviruses.

As used herein, the term "Togavirus" refers to a general classification of membrane containing viruses which include the Alphaviruses.

As used herein, the term "membrane bilayer" refers to a structure consisting of opposed amphiphatic phospholipids. The bilayer is organized in cross section from polar head groups to non-polar carbon chains to nonpolar carbon chains to polar head groups.

As used herein, the term "glycoprotein transmembrane region" refers to the amino acid sequence of the region of a membrane-integrated protein which spans the membrane bilayer.

As used herein, the term "viral vaccine" refers to a strain of virus or virus mutant which has the antigenic properties of the virus but cannot produce disease.

As used herein the term "immune surveillance" refers to a process by which blood lymphocytes survey the cells and tissues of a mammal to determine the presence of foreign (virus) proteins and stimulates the production of lymphocytes capable of targeting cells producing the foreign protein for destruction. This process also leads to the production of circulating antibodies against the foreign protein.

As used herein, the term "infectious virus particles" refers to viruses which are capable of entering a cell and producing virus protein, whether or not they are capable of producing progeny virus.

As used herein, the term "non-infectious virus particles" refers to viruses which are not capable of infecting or entering a cell.

As used herein, the term "vertebrate cells" refers to any mammalian cell.

As used herein, the term "invertebrate cells" refers to any insect cell.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning:" A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

The vaccines of the present invention are based on deletion mutations in the transmembrane domains of membrane glycoproteins of membrane-enveloped viruses. Many membrane-coated viruses have membrane glycoproteins on their surface which are responsible for identifying and infecting target cells (Schlesinger, S. and M. J. Schlesinger, 1990). These membrane glycoproteins have hydrophobic membrane-spanning domains which anchor the proteins in the membrane bilayer (Rice et al 1982).

The membrane-spanning domains of these transmembrane proteins must be long enough to reach from one side of the bilayer to the other in order to hold or anchor the proteins in the membrane. Experiments have shown that if the domains are shortened by the deletion of amino acids within the domain, the proteins do not appropriately associate with the membrane and fall out (Adams and Rose, 1985).

Unlike mammalian cell membranes, the membranes of insect cells contain no cholesterol (Clayton 1964, Mitsuhashi et al 1983). Because insects have no cholesterol in their membranes, the insect-generated viral membrane will be thinner in cross section than the viral membranes generated from mammals. Consequently, the membrane-spanning domains of proteins integrated into insect membranes do not need to be as long as those integrated into the membranes of mammals. It is possible, therefore, to produce deletions in engineered viruses which remove amino acids from the transmembrane domain of the viral glycoprotein. This results in a glycoprotein which can integrate normally into the membrane of a virus replicating in an insect cell, but not into the membrane of a virus replicating in a mammal. Thus, the mutated virus can replicate and be produced in insect cells as well as the parent wild-type virus. On the other hand, the mutant virus can infect mammalian cells and produce viral proteins; however, since the mutated virus glycoprotein cannot span and be anchored in the mammalian membrane, progeny virus cannot be produced in mammalian cells. An advantage to the approach of the present invention is that the mutants are engineered as deletion mutants, hence there is absolutely no chance for reversion to wild-type phenotype, a common problem with virus vaccines.

The protocol described by the present invention works for any virus which replicates in insects and mammals and h as integral membrane proteins as part of its structure, namely, Togaviruses, Flaviviruses and Bunya viruses and all other enveloped viruses which can replicate naturally in both mammalian and insect cells, as well as enveloped viruses which can be made to replicate in mammalian and insect cells by genetic engineering of either the virus or the cell.

Vaccines are made against any membrane-containing virus by removing amino acids from the membrane-spanning domain of a protein in the viral envelope. This is done by removing bases from a cDNA clone of the virus as described below. RNA transcribed from the altered clone is transfected into insect cells. The viruses produced are amplified by repeated growth in insect cells until large quantities of mutant viruses are obtained. These viruses are tested for its ability to infect and produce progeny in mammalian cells. Viruses which do not produce progeny in mammalian cells are tested for ability to produce immunity in laboratory animals. Those viruses which do produce immunity are candidates for production of human and animal vaccines by procedures known in the art.

Using the prototype of the Alphaviridea, Sindbis virus, the different compositions of insect and mammalian membranes are exploited to produce mutants which assemble efficiently in insect cells but assemble poorly in mammalian cells. The envelope glycoproteins of Sindbis virus are integrated into the membranes of the endoplasmic reticulum as a multi pass protein with 6 membrane spanning domains. There are, therefore, 6 potential targets for the production of deletion mutations which will prevent the correct integration of a transmembrane domain (TMD) (See FIG. 1). Some of these targets are less satisfactory for deletion mutagensis because they have functions other than simply anchoring the protein in the membrane bilayer. For example, transmembrane domain #1 (FIG. 1) is the signal sequence which is recognized by the Signal Recognition Particle and directs protein synthesis to the membranes of the ER. Truncating this domain would likely disturb targeting in both mammalian and insect cells. TMD #3 will become a cytoplasmic domain upon protein maturation and contains specific sequences that recognize and bind capsid protein. It has been shown that this interaction is very specific in nature and requires the sequence that is in the transmembrane domain (Liu et al., 1996; Lopez et al., 1994). TMD #3, therefore, like TMD #1 has a functional as well as a structural component. A significant deletion in this domain would likely eliminate budding in both cell systems. This leaves four transmembrane domains as targets for the production of deletions which will effect membrane integration (FIG. 1, TMD #2, #4, #5, and #6).

The 6k protein is not a component of mature virus and its function in virus assembly is not clear. In the poly protein the proper integration and orientation of 6k in the ER membrane is essential for the correct integration of E1. The transmembrane domains of 6k (TMD #4 and #5) are excellent targets for deletion mutation as failure to integrate one of these domains may cause the poly protein to integrate into the membrane in a wrong configuration or cause the failure to integrate E1. Transmembrane domain #2 and #6 are the membrane spanning domains of E2 and E1 and are both obvious targets for deletion mutation. Multiple membrane spanning domains in this poly protein suggest that if deletion mutations in a single transmembrane domain do not totally block virus production in mammalian cells, then deletions in additional membrane spanning domains can further reduce maturation to negligible levels.

The present invention is directed to a genetically engineered membrane-enveloped virus comprising a transmembrane protein which has a deletion of one or more amino acids in the transmembrane region of the protein such that the transmembrane protein is able to span or correctly integrate into the membrane of an infected cell when the engineered virus replicates in insect cells, but is unable to span or integrate into the membrane of an infected cell when the virus replicates in mammalian cells. Preferably, the virus is an Arthropod vectored virus selected from the group consisting of Togaviruses, Flaviviruses, Bunya viruses and all other enveloped viruses which can replicate naturally in both mammalian and insect cells, as well as enveloped viruses which can be made to replicate in mammalian and insect cells by genetic engineering of either the virus or the cell. Representative examples of such engineered viruses are ΔK391 virus, TM17 and TM16 virus. Still preferably, the insect cells are mosquito cells, such as Aedes albopictus cells, and the mammalian cells are human cells.

In a preferred embodiment, the genetically engineered, membrane-enveloped virus is Sindbis virus, and the transmembrane protein is viral glycoprotein E2. However, a person having ordinary skill in this art could readily predict that similar mutations can b e successfully installed in the membrane spanning domains of other virus membrane proteins such as E1.

In another preferred embodiment, the genetically engineered membrane-enveloped virus is selected from the group consisting of HSV, HIV, rabies virus, Hepatitis, and Respiratory Syncycial virus, and the transmembrane protein is selected from the group consisting of glycoprotein E1, glycoprotein E2, and G protein.

In still another preferred embodiment, the genetically engineered membrane-enveloped virus are RNA tumor viruses, and the transmembrane protein is Env.

The present invention is also drawn to a method of producing a viral vaccine from the genetically engineered membrane-enveloped virus disclosed herein for vaccination of mammals, comprising the steps of introducing the engineered virus into insect cells and allowing the virus to replicate in the insect cells to produce a viral vaccine. Representative examples of the engineered viruses are ΔK391 virus, TM17 virus and TM16 virus.

In addition, the present invention provides a method for vaccination of an individual in need of such treatment, comprising the steps of introducing the viral vaccine of the present invention into the individual and allowing the vaccine to produce viral proteins for immune surveillance and stimulate immune system for antibody production in the individual.

Furthermore, the present invention provides a method of producing a viral vaccine to a disease spread by a wild mosquito population to a mammal, comprising the steps of genetically engineering a deletion of one or more amino acids in a viral transmembrane protein to produce an engineered virus, wherein the transmembrane protein is able to span the membrane envelope when the virus replicates in mosquito cells, but is unable to span the membrane envelope when the virus replicates in mammalian cells, and wherein the virus remains capable of replicating in mosquito cells; introducing the engineered virus into a wild mosquito population; and allowing the virus to replicate in cells of the wild mosquito population to produce a population of mosquitos which excludes the wild type pathogenic virus and harbors the vaccine strain of the virus such that the mosquito bite delivers the vaccine to a mammal bitten.

It is contemplated that pharmaceutical compositions may be prepared using the novel mutated viruses of the present invention. In such a case, the pharmaceutical composition comprises the novel virus of the present invention and a pharmaceutically acceptable carrier. A person having ordinary skill in this art readily would be able to determine, without undue experimentation, the appropriate dosages and routes of administration of this viral vaccination compound. When used in vivo for therapy, the vaccine of the present invention is administered to the patient or an animal in therapeutically effective amounts, i.e., amounts that immunize the individual being treated from the disease associated with the particular virus. It will normally be administered parenterally, preferably intravenously or subcutaineusly, but other routes of administration will be used as appropriate. The amount of vaccine administered will typically be in the range of about $10^3$ to about $10^6$ pfu/kg of patient weight. The schedule will be continued to optimize effectiveness while balancing negative effects of treatment. See Remington's Pharmaceutical Science, 17th Ed. (1990) Mark Publishing Co., Easton, Penn.; and *Goodman and Gilman's: The Pharmacological Basis of Therapeutics* 8th Ed (1990) Pergamon Press; which are incorporated herein by reference. For parenteral administration, the vaccine will be most typically formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin.

The following examples are given for the purpose of illustrating various embodiments of the invention and are not meant to limit the present invention in any fashion:

EXAMPLE 1

A Single Amino Acid Deletion Mutant, K391

Using the full length clone of the Alpha virus Sindbis described previously (Liu et al 1996, Rice et al., 1987), a deletion removing 3 bases encoding a lysine at position 391 in the amino acid sequence of the virus glycoprotein E2 has been constructed. This lysine is part of the putative membrane-spanning domain of this protein (Rice et al 1982).

Site-directed mutagenesis was used to generate a deletion mutant (Lys391) in Toto 1101, a plasmid containing the full-length Sindbis cDNA and an SP6 promoter that can be used to transcribe infectious RNA from the clone in vitro (Rice et al., 1987; Liu and Brown, 1993a). Using the megaprimer method of PCR mutagenesis (Sarkar and Sommer, 1990) described previously (Liu and Brown, 1993a), three nucleotides (nucleotides 9801, 9802, 9803) were removed in the cDNA clone of Toto 1101, resulting in the removal of the codon AAA (K391).

A 30 base oligonucleotide of the sequence, 5'CTCACG-GCGCGCACAGGCACATAACACTGC3' (SEQ ID No.: 1) was used as the mutagenesis primer. This primer, along with the "forward primer" 5'CCATCAAGCAGTGCGTCG3' (SEQ ID No.: 2; 18 mer), generated a 518 base "Megaprimer" (nucleotides (nts) 9295–9813). The second PCR reaction consisted of 0.5 µg of megaprimer, 100 µg Toto 1101 template and 0.5 µg of the "reverse primer" 5' GGCAGTGTCCACCTTAATCGCCTGC 3' (SEQ ID No.: 3). All PCR reactions employed 30 cycles at 95 degrees for 1 min., 64 degrees for 1 min., 72 degrees for 1 min. and a final incubation at 72 degrees for 8 min. The resulting PCR product (1149 nts) was cleaved with BCL I and SPL and inserted into the corresponding site in Toto 1101, creating the deletion mutant K391. After the deletion was confirmed by dideoxynucleotide sequencing through the entire subcloned region using Sequenase™ (U.S. Biochemical, Cleveland, Ohio.), infectious RNA was transcribed in vitro using SP6 polymerase and was introduced into BHK-21 cells.

EXAMPLE 2

In Vitro Transcription and RNA Transfection Of K391

Plasmid DNA containing the full-length cDNA copy of Sindbis virus K391 or wild type RNA was linearized with XhoI and transcribed in vitro with SP6 RNA polymerase as described previously (Rice et. al., 1987). 1 µg of Xho I linearized K391 cDNA or wild type Sindbis virus cDNA was transcribed in buffer consisting of 80 mM Hepes, pH 7.5, 12 mM MgCl, 10 mM DTT, 2 mM spermidine and 100 µgm BSA with 3 mM each ATP, UTP, CTP, 1.5 mM GTP and 4.5 mM $m^7$ GpppG, 20 units SP6 RNA polymerase and 20 units RNase inhibitor in a 20 µl reaction volume. After incubation at 37° C. for 2 hours, RNA production was assayed by running 2 µl of the RNA product on a 1% agarose gel.

Baby Hamster Kidney (BHK21) cells and Aedes albopictus (mosquito) cells were transfected with RNA derived from the mutant or wild type clone. Mosquito cell transfections were carried out using 5×10$^6$ cells resuspended in RNase free electroporation buffer consisting of 20 mM Hepes pH 7.05, 137 mM NaCl, 0.7 mM $Na_2HPO_4$ and 6 mM dextran. Washed cells were resuspended in diethyl pyrocarbonate (DEPC) treated water to a concentration of $5 \times 10^7$ cells/ml. RNA transcripts in 20 µl were added to 400 µl washed cells and transferred to a 0.2 cm gap length cuvette. Optimal electroporation parameters for these cells was found to be 2 KV 25 µF, 8 resistance. Transfected cells were incubated at 37° C. until cytopathic effect was observed (about 24 hours).

After 24 hours of incubation, the media was collected from both infected cell lines as well as non-RNA transfected controls. The media from each cell line was tested for the presence of infectious virus by plaque assay (as described by Renz and Brown 1976) on mosquito and BHK-21 cell monolayers (Table 1).

TABLE 1

Infectious virus produced by transfection of BHK21 or *Aedes albopictus* (AA) cells with Sindbis virus wild type (wt) or mutant K391

| Cell line Transfected | BHK Mock[a] Transfected | BHK with wt RNA | BHK with K391 RNA | AA Mock Transfected | AA with wt RNA | AA with K391 RNA |
| --- | --- | --- | --- | --- | --- | --- |
| Media titered on BHK | no virus detected | $1.5 \times 10^9$ virus/ml | $3.0 \times 10^3$ | no virus detected | $5.0 \times 10^8$ virus/ml | $1.0 \times 10^8$ |
| Media titered on AA | no virus detected | $8 \times 10^7$ virus/ml | $8.0 \times 10^4$ | no virus detected | $1.0 \times 10^9$ virus/ml | $2.0 \times 10^9$ virus/ml |

[a]Mock indicates that transfection protocol was carried out without RNA

As shown in Table 1, the mutant K391 produces significant amounts of infectious virus particles only when replicating in the insect cell. BHK cells transfected with K391 produced very low levels of virus, 4 to 5 orders of magnitude lower than the amount produced in insect cells.

EXAMPLE 3

Metabolic Radioactive Labeling of Viral Proteins

Subconfluent monolayers of BHK21 cells in 25 $cm^2$ flasks were transfected with wild type or K391 mutant RNA as described above. Monolayers were starved for 30 min in methionine- and cysteine-free medium (MEM-E) containing 1% FCS, 2 mM glutamine and 5% TPB (starvation medium). At 16 hours post-transfection, cells were pulse-labeled with starvation medium containing 50 µCi/ml [$^{35}$S] Met/Cys protein labeling mix for 20 minutes. Labeling was terminated by washing the monolayers with PBS containing 75 µg/ml cycloheximide. Monolayers were chased for 45 minutes in medium containing 10 times the normal concentration of methionine and cysteine and 75 µg/ml cycloheximide.

EXAMPLE 4

Immunoprecipitation and Polyacrylamide Gel Electrophoresis

Radiolabeled viral proteins were immunoprecipitated with antisera as described (Knipfer and Brown, 1989). [$^{35}$S] Met/Cys labeled cells were washed twice in cold PBS and lysed in lysis buffer: 0.5% NP-40, 0.02 M Tris HCl pH 7.4, 0.05 M NaCl, 0.2 mM PMSF, 0.2 mM TPCK and 0.02 mM TLCK. The nuclei were pelleted by centrifugation and discarded. The supernatant was pre-absorbed with 100 µl of protein A/Sepharose beads (Sigma) suspended in lysis buffer for 1 hr, and the beads were pelleted. The pre-absorbed supernatant was treated with 200 µl of protein A/Sepharose beads coupled to rabbit anti-SVHR serum or E2 tail mono-specific polyclonal serum and agitated overnight at 4° C. The immunoprecipitated bead-antibody-protein complexes were washed three times with lysis buffer and then solubilized in SDS-PAGE sample buffer consisting of 12% glycerol, 4% SDS, 50 mM Tris pH 6.8, 5% mercaptoethanol and 0.02% bromphenol blue. The samples were heated for 3 min at 95° C. and the beads were removed from the sample by centrifugation. Gel electrophoresis was carried out on a 10.8% SDS-PAGE or 16% Tricine gel as described previously (Liu and Brown, 1993 a,b). Fluorography was performed as described (Bonner and Laskey, 1974) and dried gels were exposed to Kodak XAR-5 film (see FIG. 2).

EXAMPLE 5

Transmission Electron Microscopy

BHK-21 cell monolayers infected with K391 produced from transfected mosquito cells or transfected with K391 RNA were lifted from flasks by trypsin treatment at desired time points, and the cells were pelleted by low speed centrifugation. Cell pellets were washed twice in PBS and fixed in 4% glutaraldehyde at 4° C. overnight. The cells were then washed three times with 0.2 M cacodylate buffer (pH 7.2), post-fixed with 2% osmium tetroxide for 1 hour at room temperature, and washed three times in cacodylate buffer. The cells were stained en bloc for 1 hr at room temperature with 0.5% uranyl acetate. After three washes, cell pellets were embedded in 1% agarose and dehydrated through a graded ethanol/acetone series. Final embedding was in Mollenhauer's (1964) Epon-Araldite epoxy mixture #1 at 70° C. for two days. Ultrathin sections were cut on a Sorvall MT5000 microtome and collected on 150 mesh copper grids. Sections were stained with 1% uranyl acetate and/or lead citrate and were photographed in a Jeol 100CX transmission electron microscope (see FIG. 3).

Figure 2:
FIG. 2 shows the results of radiolabeled Sindbis virus proteins recovered from transfected tissue-cultured cells. BHK-21 cells mock transfected (1), transfected with mutant Δ391 RNA (2), and Aedes albopictus cells transfected with Δ391 RNA (3), were labeled with radioactive amino acids as described in Example 3. At 24 hours post-transfection, proteins were precipitated with virus specific anti-serum as described in Example 4. The figure shows that both BHK-21 cells and Aedes albopictus cells transfected with RNA of the deletion mutant produce the three viral structural proteins E1, E2, and C which are not detected in the mock transfected cells.
Figure 3A:
FIGS. 3A and 3B are electron micrographs of BHK-21 cells (FIG. 3A) and Aedes albopictus cells (FIG. 3B) transfected with RNA of the Sindbis virus deletion mutant Δ391. Cells were transfected as described in Example 2. BHK-21 cells (FIG. 3A) show clusters of virus core structures in the cell cytoplasm (A) even though these cells produce very low levels of mature virus (Table 1). Aedes albopictus cells (FIG. 3B) also produce clusters of virus cores; however, these cores are found free in the cells' cytoplasm similar to those in BHK-21 cells (A) and are also found associated with cell membranes (B). This latter case is not found in BHK-21 cells, indicating that the glycoproteins E1 and E2, although present, do not function to bind them.
Figure 3B:
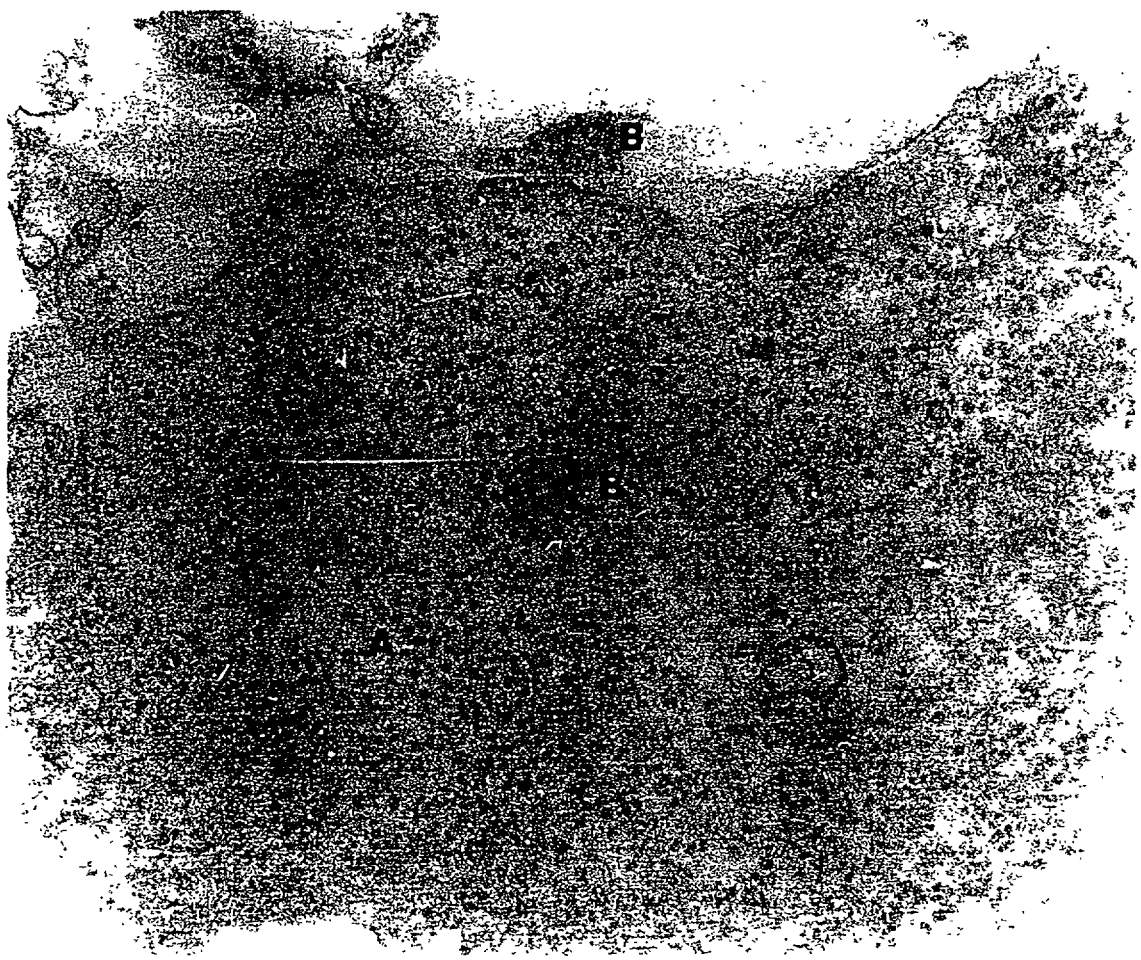

Although BHK cells infected with K391 virus or transfected with K391 RNA produce no virus detectable by the plaque assay, it was shown by PAGE that they do produce all virus structural proteins (FIG. 2). Further, it was shown by electron microscopy that they assemble the intracellular (non infectious) virus cores (FIG. 3).

Delta K391 produces very high titers of mutant Sindbis virus particles when allowed to replicate in mosquito cells. The exposed regions of the proteins (ecto domains) are wild type in sequence. These wild type proteins allow the virus to enter mammalian cells and produce virus proteins (see FIG. 2) but new virus is not assembled as shown by electron microscopy in FIG. 3.

Delta K391 is a vaccine strain. It is produced in very high concentration in cultured insect cells. When the virus is injected into a mammalian host, the virus circulates and infects cells in the mammalian host. These infected cells produce and present virus proteins for immune surveillance. However, the infection will be limited primarily to those cells infected initially by the innoculum because of the truncation in the membrane domain of the viral glycoprotein. Because the vaccine strain is the result of a deletion mutation, reversion to wild type pathogenic phenotype is not possible.

Furthermore, an engineered deletion mutant may be introduced into the wild mosquito population. It has been shown that these viruses are spread from the female parent to the progeny by a process of transovariol transmission (Leakey 1984). When these mosquitoes bite a vertebrate they will provide an immunizing dose ($10^6$ infectious particles) of the vaccine strain (for example, Delta K391). Karpf et al (1997) showed that infection of insect cells by one Alpha virus prevents the cells from being infected by another, even distantly-related alpha virus for an indefinite amount of time (over two years in cell culture, where the life of a mosquito is 28 days). Thus, the presence of the vaccine strain such as K391 or other deletion mutants described in the present invention will block the spread of other related and pathogenic viruses by these insects

EXAMPLE 6

Deletion In The E2 Transmembrane Domain

Protocols for testing the requirements placed on the transmembrane domain of E2 (FIG. 1, TMD #2) is given. This protocol can be easily replicated for any other of the Sindbis membrane spanning domains or the membrane spanning domains of any other virus glycoprotein. The hydrophobic Sindbis PE2 membrane anchor consists of 26 amino acids. As is common with other membrane spanning domains little amino acid homology is conserved among the alphaviruses, although the length of this hydrophobic region is highly conserved (Strauss and Strauss, 1994). The lack of sequence conservation in this domain suggests that it is the hydrophobic properties of the domain and not its sequence which is critical for integration.

The transmembrane domain of E2 begins at amino acid 365 of the PE2 sequence. This hydrophobic region consists of the sequence: VYTILAVASATVAMMIGVTVAVLCAC (SEQ ID No.: 4). Adams and Rose (1985) demonstrated that a minimum of 14 amino acids in the transmembrane domain of the VSV G protein were necessary for proper anchoring in mammalian cells. Therefore, mutagenic primers have been designed which create a nested set of deletions in the E2 transmembrane domain. Beginning with a deletion of 16 amino acids (which leaves 10 amino acids in the hydrophobic region), a set of deletions were constructed which delete from as many as 16 amino acids, to as few as 1 amino acid from the membrane anchor (FIG. 4).

Deletions were constructed using PCR megaprimer mutagenesis to generate deleted fragments containing unique BclI and SplI sites. All resulting constructs were installed into the wild-type Sindbis cDNA construct Toto Y420 to generate the mutant plasmids. After linearization with XhoI and transcription using SP6 polymerase, transcripts were transfected into BHK or Aedes albopictus cells by electroporation as described above. Production of infectious virus from these transfections were titered on both BHK and C710 mosquito cells to determine the host range of these constructs. Table 2 shows the deleted sequences and the primer sequences used in their construction.

For each construct the same primer pair is used to generate the entire BclI to SplI region. The forward primer E1Bcl21 is comprised of the sequence from nucleotide 9306–9327 and reads from 5'–3' GCGTCGCCFATAA-GAGCGACC (SEQ ID No.: 5). The reverse primer Splext is comprised of the sequence from nucleotide 10420–10444 which is the complementary sequence reading from 5'-3' CAGTGTGCACCTTAATCGCCTGC (SEQ ID No.:6).

The virus produced by transfection of insect cells is tested for its ability to produce plaques in BHK and C7-10 mosquito cells as for the mutant E2 ΔK391. Those mutants which do not produce plaques in BHK cells are tested for their ability to infect BHK cell relative to wild type virus by immunofluorescence assay of infected monolayers. This later assay is compared to the total protein in purified preparations of the mutant and wild type virus to establish the relative infectivity of each mutant population. The goal is to truncate the transmembrane domain as much as possible and still obtain reasonable amounts of virus in C7-10 mosquito cell monolayers which can infect but not produce mature virus in BHK cells. Additional transmembrane domains (up to four domains) can be truncated in circumstances where truncation of a single transmembrane domain reduces but does not eliminate virus growth in BHK cells.

The length of the transmembrane (TM) domain of E2 was systematically reduced from 26 amino acids to 10, 12, 14, 16, 17 and 18 amino acids, and the effects of these truncations on the ability of these viruses to replicate in cells of the vertebrate (BHK-21, hamster cells) and invertebrate (Aedes albopictus, mosquito cells) hosts were examined. Table 3 presents results typical of several of such experiments. The data reveal that reducing the transmembrane domain from 26 to 10 amino acids or 12 amino acids results in viruses incapable of efficient assembly in either host. Increasing the length of the transmembrane domain to 14 amino acids results in viruses that grow poorly in mammalian cells but somewhat better in insect cells. Increasing transmembrane domain length to 16 or 17 amino acids restores wild type levels of growth in insect cells while growth in mammalian cells remains greatly impaired. Increasing the length of the transmembrane domain to 18 amino acids restores growth in mammalian cells. The reduction in the length of the transmembrane domain of the E2 glycoprotein has resulted in the production of virus mutants in which efficient growth is restricted to insect cells. The accepted terminology for such mutations is "host range mutation".

The data presented above show that large deletions in the transmembrane domains of the glycoproteins of insect vectored viruses can result in the restriction of virus assembly to insect cells. Mutants which produce low levels of virus (transmembrane domains 10, 12, 14) are unable to correctly integrate the membrane proteins into the host cell membranes. The less impaired mutants, represented by transmembrane domain 16 and transmembrane domain 17, can infect mammalian cells, produce structural proteins, and form nucleocapsid structures containing the viral RNA. However, these mutants are defective in steps in virus assembly.

TABLE 2

Listing of the deletions in Sindbis E2 and the primers used

| Primer-Designated by No. of Transmembranal Amino Acids | Nucleotides Deleted | Oligonucleotide Sequence of Mutagenic Primer (Negative Strand) |
|---|---|---|
| E2 TM10 | 9734–9782 | ACATAACACTGCGATGGTGTACAC (SEQ ID No.: 7) |
| E2 TM12 | 9740–9782 | ACATAACACTGCGGCTAAGATGG (SEQ ID No.: 8) |

TABLE 2-continued

Listing of the deletions in Sindbis E2 and the primers used

| Primer-Designated by No. of Transmembranal Amino Acids | Nucleotides Deleted | Oligonucleotide Sequence of Mutagenic Primer (Negative Strand) | |
|---|---|---|---|
| E2 TM14 | 9746–9782 | ACATAACACTGCTGCGACGGCT | (SEQ ID No.: 9) |
| E2 TM16 | 9743–9773 | GCAACAGTTACGACGGCTAAG | (SEQ ID No.: 10) |
| E2 TM17 | 9743–9770 | ACAGTTACGCCGACGGCTAAG | (SEQ ID No.: 11) |
| E2 TM18 | 9743–9767 | GTTACGCCAATGACGGCTAAG | (SEQ ID No.: 12) |
| E2 TM19 | 9743–9764 | CGCCAATCATGACGGCTAAGA | (SEQ ID No.: 13) |
| E2 TM20 | 9755–9773 | GCAACAGTTACGGTAGCTGA | (SEQ ID No.: 14) |
| E2 TM21 | 9755–9770 | AGTTACGCCGGTAGCTGA | (SEQ ID No.: 15) |
| E2 TM22 | 9761–9773 | TGCAACAGTTACCGCCACGGT | (SEQ ID No.: 16) |
| E2 TM23 | 9761–9770 | ACAGTTACGCCCGCCACGGT | (SEQ ID No.: 17) |
| E2 TM24 | 9761–9767 | GTTACGCCAATCGCCACGGT | (SEQ ID No.: 18) |
| E2 TM25 | 9761–9764 | ACGCCAATCATCGCCACGGT | (SEQ ID No.: 19) |

TABLE 3

Growth of Sindbis virus TM deletion mutants in insect and vertebrate cells

| Mutant⁰ | Growth in insect cells (pfu/ml)– | Growth in mammalian cells (pfu/ml)– |
|---|---|---|
| Wild type | $5 \times 10^9$ | $5 \times 10^9$ |
| TM 10 | $2 \times 10^3$ | $3 \times 10^4$ |
| TM 12 | $5 \times 10^3$ | $6 \times 10^2$ |
| TM 14 | $6 \times 10^7$ | $4 \times 10^2$ |
| TM 16 | $2 \times 10^9$ | $7 \times 10^4$ |
| TM 17 | $3 \times 10^9$ | $1 \times 10^5$ |
| TM 18 | $1 \times 10^8$ | $6 \times 10^8$ | both cell types were assayed by titration on monolayers of BHK cells.

EXAMPLE 7

Uses of Deletion Mutants as Vaccine

Mutations which restrict the assembly of virions only to insect cells suggest that viruses produced from these cells may be used to infect an animal which could only produce low numbers of progeny viruses. Such a phenotype could result in the production of protective immunity in that animal without pathological Id consequences. Mutants TM 16 and 17 were selected for further study to determine their potential for producing protective immunity. The results of these experiments are presented in Table 4.

TABLE 4

Protection Of Adult Mice From Sindbis Virus By Vaccination With TM Mutations

| VIRUS | DOSE | MORTALITY | MORBIDITY | CHALLENGE | Morbidity POST CHALLANGE | Mortality POST CHALLENGE |
|---|---|---|---|---|---|---|
| Mock (buffer) | $10^6$ | 0% | 0% | SAAR86 1000 pfu i.c. | 92% | 36% |
| TM16 | $10^6$ | 0% | 0% | SAAR86 1000 pfu i.c. | 68% | 48% |
| TM16 UV | NA | 0% | 0% | SAAR86 1000 pfu i.c. | 92% | 36% |
| TM17 | $10^6$ | 0% | 0% | SAAR86 1000 pfu i.c. | 0 | 0 |
| TM17 UV | NA | 0% | 0% | SAAR86 1000 pfu i.c. | 84% | 36% |

Mutants were constructed using the Stratagene Quick change® mutagenesis protocol using a cDNA template containing the virus structural genes. Desired mutations were subcloned into the full length virus cDNA vector containing an SP6 promoter for the transcription of full length infectious viral RNA. Mutant transcripts were transfected into—mosquito cells or—mammalian BHK cells and incubated for the appropriate time and temperature before harvesting the virus-containing media. Virus yields from Twenty five 21 days old CD-1 mice were used in each study. Mutant viruses from transfected Aedes albopictus U4.4 cells was injected into the mice subcutaneously at the dose indicated. Fourteen days after the initial injection the mice were challenged with the SAAR 86 strain of Sindbis virus as indicated.

TM 16 was a poor vaccine compared to TM 17 although both mutations showed identical phenotypes in the tissue culture cell system described in Table 3. It is clear that the protection achieved by injection with TM 17 was not the simple result of exposure to virus protein, as the UV treated virus did not protect.

To further elucidate the mouse response to these two mutants, serum of vaccinated mice was tested for the presence of circulating antibody by standard ELISA assay. The results of this experiment is shown in FIG. 5.

Mutants TM16 and TM 17 appeared to produce similar levels of circulating antibody as would be expected from an inoculation with the same quantity of virus. This result suggested that antibodies capable of binding to denatured virus, as well as infectious virus, were induced in the mice at roughly equivalent levels by both mutants.

Figure 5:
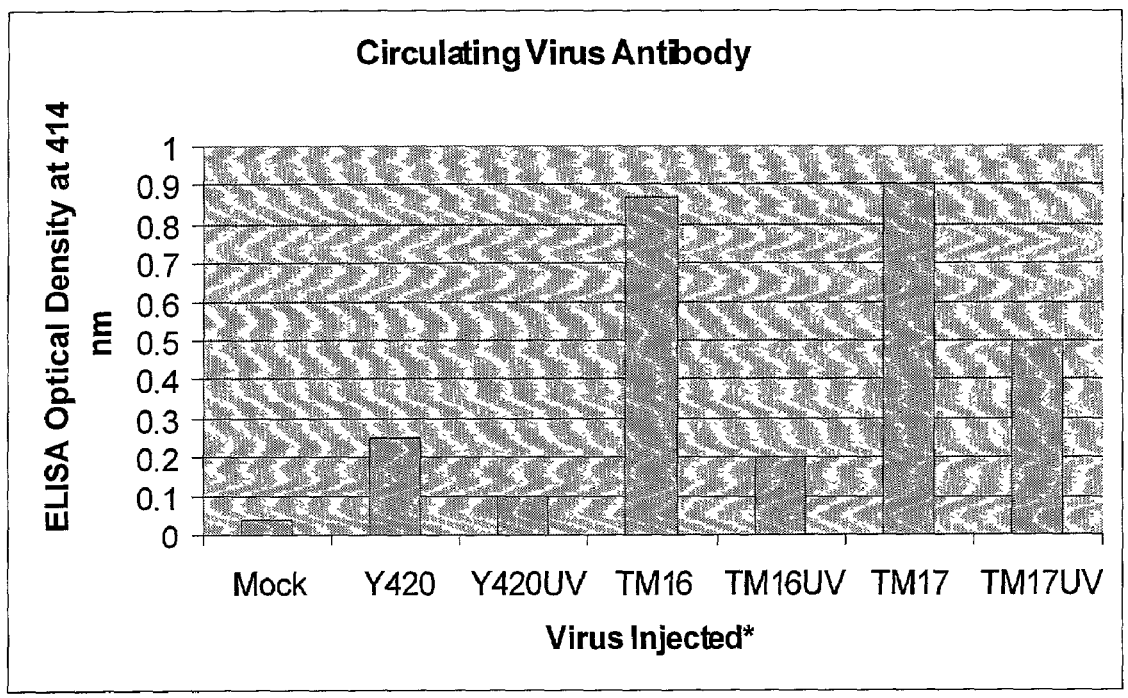
FIG. 5 shows circulating Sindbis virus antibody determined by ELISA. Mutant viruses from transfected mosquito U4.4 cells were injected into 25 adult CD-1 mice to establish the protective index (Table 4). Injections of live mutants and UV inactivated viruses were repeated into 3 additional mice to determine Ab titers by standard ELISA. The results presented are from a $10^{-2}$ dilution of mouse serum.
Figure 6:
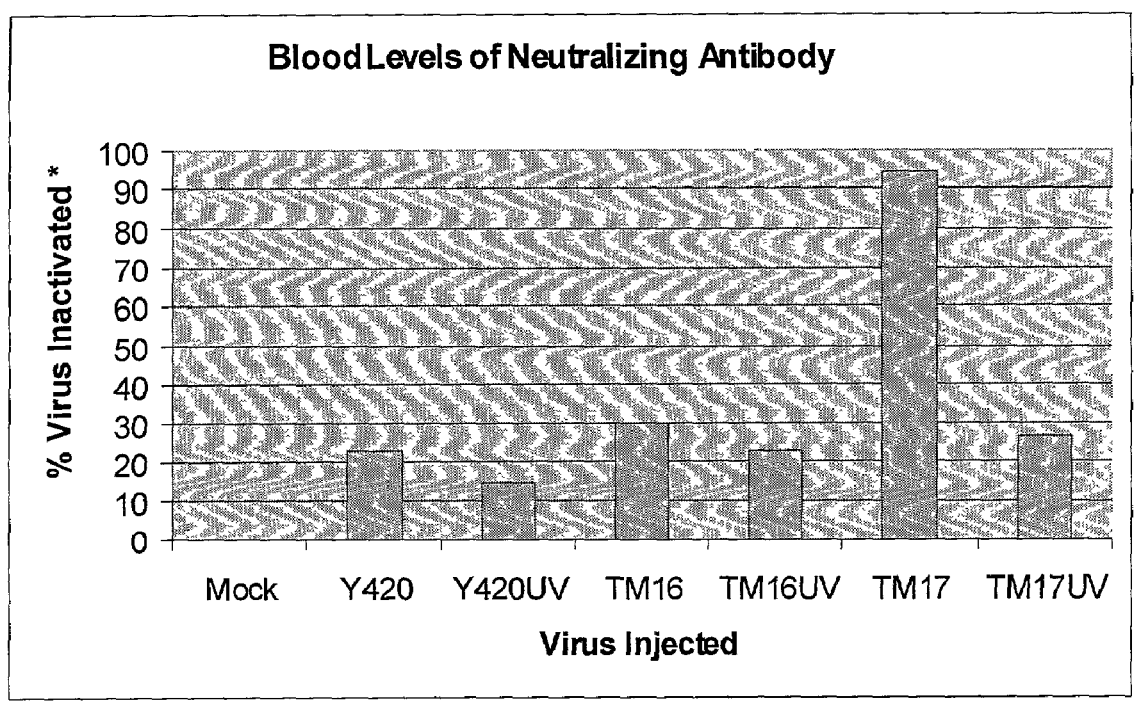
FIG. 6 shows circulating neutralizing antibody. Antiserum used in the experiment described in FIG. 5 was also assayed for neutralizing Ab. The neutralizing Ab data presented represent the % of wild type infectious virus inactivated by a $10^{-2}$ dilution of serum from 3 adult CD-1 mice.

The results presented in FIG. 5 suggested that the immune response to TM 17 was different from the response to TM16. The serum of the vaccinated mice was therefore examined for the presence of neutralizing antibody to Sindbis virus. The results are shown in FIG. 6. By contrast with mutant TM16, mutant TM 17 induced significantly more neutralizing antibody. This likely explains its superior performance as a vaccine.

The transmembrane domains of the glycoproteins of Alpha, Flavi and Bunya viruses which have been sequenced reveal that they have the common property of being hydrophobic sequences that are predicted to form alpha helices in membrane bilayers. It is predicted that truncation of the transmembrane domain described above for an alphavirus will produce a similar pattern of host restriction in any one of these viruses. Thus, the protocol described above has the potential of producing live vaccines against any one of these agents. Because the mutations are large deletions, there is little prospect of spontaneous reversion to wild type virus. Indeed, in the time these mutants were examined in the laboratory, no such revertants have been detected.

The observation that TM16 and 17 have such different properties in terms of their ability to produce protection as a vaccine while having similar growth characteristics in cell culture is most interesting. The data showing that TM 17 produces a higher level of neutralizing antibody suggests that TM 17 may be structurally more identical to wild type virus than TM 16. A possible explanation for this may lie in the very precise structure of the virion itself. The surface of Sindbis is a T=4 icosahedral shell made rigid by scaffolding interaction among the E1 glycoproteins. In the mature virion, the E1 glycoprotein is a highly constrained energy-rich metastable structure. The energy stored in E1 is believed to be used to disassemble the protein lattice and to allow virus-cell membrane fusion. The constrained form of E1 is developed in the endoplasmic reticulum of infected cells by folding through several disulfide bridged intermediates as the PE2-E1 heterotrimer is produced. The energy rich form of E1 rapidly reorganizes to a lower energy state by the reshuffling of disulfide bridges if the protein is isolated from the virion in the absence of thiol blocking agents. It has also been demonstrated that the function of the membrane glycoprotein is affected by mutations in the core protein, suggesting that specific interactions between the capsid and the membrane protein E2 are critical to virus stability. The rigid organization of the virus membrane glycoproteins and the identical structure of the inner core may require the E2 endodomain (cytoplasmic location), which binds to the virus core via interactions with the capsid protein hydrophobic pocket, emerges from the membrane in a particular orientation. The correct orientation may be required for the very specific binding of the E2 endodomain to the hydrophobic cleft in the capsid protein. As amino acids are removed from the transmembrane domain helix, the orientation of the E2 tail may be altered at the point of egress from the membrane bilayer.

Alternatively, deletions in the transmembrane domain of Sindbis E2 may distort the E2 ectodomain, the domain oriented toward the exterior of the cell, thereby destabilizing interactions with the scaffolding protein E1. In the case of TM 16, this may result in an association that allows for virus assembly but which produces a relatively unstable virion. This instability may result in the spontaneous reshuffling of disulfide bridges in the E1 glycoprotein to a low energy, non-native state which is antigenically dissimilar from native protein and may cause the structural degradation of the virion. The E2 tail of the mutant TM 17 contains an additional amino acid in the transmembrane domain helix and is predicted to exit the membrane at a position 100° distant to that of the TM 16 mutant. This may relieve sufficient structural strain to allow the mutant to remain stable and immunogenic.

In summary, differences in the structure and physical properties of insect and mammalian cells have been exploited to produce host range mutations with potential as vaccines. This approach should be applicable to the production of vaccines against any of the several hundred membrane-containing insect borne viruses for which a cDNA clone can be produced.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The following references were cited herein:

Adams and Rose. (1985) Cell 41(3):1007–15.

Berge (ed.) (1975): *International Catalogue of Arboviruses;* 2nd ed., DHEW Publ. No. (CDC) 75–8301 (U.S. Government Office, Washington, D.C.)

Bonner and Laskey. (1974). Eur. J. Biochem. 46:83–88.

Bowers et al. (1995). Virology 212: 1–12.

Brown and Condreay (1986). Replication of alphaviruses in mosquito cells. In The Togaviridae and Flaviviridae. S. Schlesinger (ed.), pp. 473–501.

Clayton. (1964) J. Lipid Res. 5:3–19.

Karpf et al. (1997) J. Virol.71:7119.

Knipfer and Brown. (1989). Virology 170:117–122.

Leake. (1984). Transovarial transmission of arboviruses by mosquitoes. In Vectors in Virus Biology (Mayo and Harrap, eds.), pp. 63–92. Academic Press.

Liu and Brown (1993a). J. Cell Biol. 120:877–883.

Liu and Brown (1993b). J. Virol., 196:703–711.

Liu et al. (1996) Virology 222: 236–246.

Mitsuhashi et al. (1983). Cell Biol. Int. Rep. 7:1057–1062.

Mollenhauer. (1964). Stain Techn. 39:111–114.

NIAID Report of the Task Force on Microbiology and Infectious Diseases (1992). NIH Publication No. 92-3320.

Renz and Brown. (1976). J. Virol. 19:775–781.

Rice et al. (1982). J. Mol. Biol. 154:355–378.

Rice et al. (1987). J. Virol. 61:3809–3819.

Sarkar and Sommer. (1990). BioTechniques. 8:404–407.

Schlesinger and Schlesinger (1990). "Replication of Togaviridae and Flaviviridae." (D. M. Knipe and B. N. Fields, eds.), In Virology Vol. I, pp. 697–711. Raven Press, Ltd., New York.

Sprenger and Wuithiranyagool (1985). J. Am. Mosquito Control Assoc. 2:217–219.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A genetically engineered Arbovirus comprising, a transmembrane glycoprotein with a deletion of one or more amino acids in a transmembrane domain wherein, said virus is capable of infecting and producing progeny virus in insect cells, wherein said engineered Arbovirus has an ability to infect mammalian cells but a reduced ability to replicate therein relative to wild type virus.

2. The genetically engineered Arbovirus of claim 1, wherein the insect cells are mosquito cells.

3. The genetically engineered Arbovirus of claim 2, wherein the mosquito cells are *Aedes ablbopictus* cells.

4. The genetically engineered Arbovirus of claim 1, wherein said virus produces at least 1,000 fold more progeny virus when infecting insect cells than when infecting mammalian cells.

5. The genetically engineered Arbovirus of claim 4, wherein said virus produces at least 10,000 fold more progeny virus when infecting insect cells than when infecting mammalian cells.

6. The genetically engineered Arbovirus of claim 1, wherein the transmembrane glycoprotein has a deletion of nine or more amino acids in a transmembrane domain.

7. The genetically engineered Arbovirus of claim 1, wherein the genetically engineered Arbovirus is a genetically engineered Togavirus, Flavivirus or Bunyavirus.

8. The genetically engineered Arbovirus of claim 7, wherein the genetically engineered Togavirus is a genetically engineered Alphavirus.

9. The genetically engineered Arbovirus of claim 8, wherein said transmembrane glycoprotein is glycoprotein E1, or glycoprotein E2.

10. The genetically engineered Arbovirus of claim 9, wherein the genetically engineered Alphavirus is a genetically engineered Sindbis virus.

11. The genetically engineered Arbovirus of claim 10, wherein said genetically engineered Sindbis virus is the TM16 virus.

12. The genetically engineered Arbovirus of claim 10, wherein said genetically engineered Sindbis virus is the ΔK391 virus.

13. The genetically engineered Arbovirus of claim 10, wherein said genetically engineered Sindbis virus is the TM17 virus.

* * * * *